United States Patent [19]

Pigerol et al.

[11] 4,317,768
[45] Mar. 2, 1982

[54] DIHYDROPYRIDINE DERIVATIVES AS STABILIZERS FOR VINYL CHLORIDE POLYMERS

[75] Inventors: Charles Pigerol, Saint-Ouen; Marie-Madeleine Chandavoine; Paul de Cointet de Fillain, both of Sisteron, all of France

[73] Assignee: Labaz, Paris, France

[21] Appl. No.: 93,861

[22] Filed: Nov. 13, 1979

Related U.S. Application Data

[63] Continuation of Ser. No. 946,351, Sep. 27, 1978, abandoned.

[30] Foreign Application Priority Data

Oct. 14, 1977 [FR] France .................... 77 30992

[51] Int. Cl.$^3$ .............................................. C08K 5/34
[52] U.S. Cl. ........................................ 524/99; 546/321
[58] Field of Search ................................. 260/45.8 N

[56] References Cited

U.S. PATENT DOCUMENTS

| | | | |
|---|---|---|---|
| 3,728,282 | 4/1973 | Barie, Jr. et al. | 252/400 |
| 3,730,943 | 5/1973 | Weisfeld et al. | 260/45.75 W |
| 3,773,773 | 11/1973 | Bossert | 546/321 |
| 3,799,936 | 3/1974 | Meyer et al. | 546/321 |
| 3,829,396 | 8/1974 | Oakes et al. | 260/23 XA |
| 4,057,530 | 11/1977 | Pigerol et al. | 260/45.8 N |
| 4,209,439 | 6/1980 | Pigerol et al. | 260/45.8 N |
| 4,214,088 | 7/1980 | Abeler et al. | 260/45.8 N |
| 4,239,893 | 12/1980 | Pigerol et al. | 260/45.8 N |

FOREIGN PATENT DOCUMENTS 2239496 2/1975 France .

Primary Examiner—Lorenzo B. Hayes
Assistant Examiner—R. A. White
Attorney, Agent, or Firm—Mason, Kolehmainen, Rathburn & Wyss

[57] ABSTRACT

The instant invention relates to compounds of the general formula:

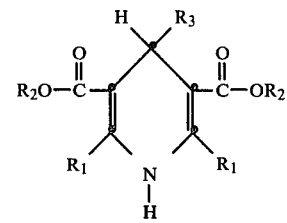

wherein $R_1$ represents an alkyl, alkenyl, phenyl or phenylalkyl radical, $R_2$ represents an alkyl, alkenyl or alkynyl radical, a ω-halogenoethyl radical, an optionally substituted benzyl radical, a phenylalkenyl radical, an optionally substituted phenyl radical, a radical of the formula $R_4$—O—$(CH_2)_n$— wherein n is 2, 3, or 4 and $R_4$ represents an optionally substituted alkyl radical or a phenyl radical, $R_3$ represents a hydrogen atom, an alkyl, alkenyl or phenyl radical.

The compounds of formula I have been found to be useful as stabilizers for vinyl resins.

9 Claims, No Drawings

DIHYDROPYRIDINE DERIVATIVES AS STABILIZERS FOR VINYL CHLORIDE POLYMERS

CROSS REFERENCE TO RELATED APPLICATION

This application is a continuation of Ser. No. 946,351 filed Sept. 27, 1978 now abandoned.

This invention relates to new additives for plastic materials and, more particularly, to new stabilizers for vinyl resins such as, for instance, polyvinyl chloride and its co-polymers.

The stabilizers with which the invention is concerned are the substances represented by the general formula:

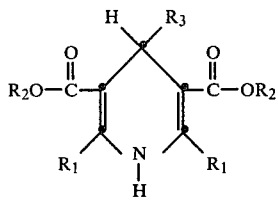

I wherein $R_1$ represents a branched-or straight-chain alkyl group containing from 1 to 16 carbon atoms, a branched- or straight-chain alkenyl group containing from 4 to 12 carbon atoms, a phenyl radical, a phenylalkyl radical in which the alkyl radical is a straight-chain alkyl group containing from 1 to 6 carbon atoms, $R_2$ represents a branched- or straight-chain alkyl group containing from 1 to 18 carbon atoms, a branched- or straight-chain alkenyl or alkynyl group containing from 3 to 11 carbon atoms, an ω-halogenoethyl group, a benzyl radical, a benzyl radical substituted on the ortho- or para-position by a halogen atom or by a methyl or methoxy radical, a phenylalkenyl radical in which the alkenyl chain contains 2 or 3 carbon atoms, a phenyl radical, a phenyl radical substituted on the para-position by a halogen atom, a methyl or methoxy radical, a radical of the formula $R_4-O-(CH_2)_n-$, wherein n is 2, 3 or 4 and $R_4$ represents a branched- or straight-chain alkyl group containing from 1 to 4 carbon atoms, unsubstituted or substituted on the ω-position by a halogen atom or by a methoxy radical, or $R_4$ represents a phenyl group, $R_3$ represents a hydrogen atom, a branched- or straight-chain alkyl group containing from 1 to 7 carbon atoms, a branched- or straight-chain alkenyl group containing from 3 to 7 carbon atoms or a phenyl radical, with the proviso that when $R_1$ represents a methyl radical and $R_3$ a hydrogen atom, $R_2$ does not represent an alkyl or a phenyl radical.

The substance of formula I which are listed hereunder are new and are claimed as such:
2,6-Dimethyl-3,5-dicarboallyloxy-1,4-dihydropyridine (1)
2,6-Dimethyl-3,5-dicarbopropargyloxy-1,4-dihydropyridine (2)
2,6-Dimethyl-3,5-di-(2'-carbochloro-ethoxy)-1,4-dihydroyridine (3)
2,6-Dimethyl-3,5-di-(4'-carbomethoxy-benzyloxy)-1,4-dihydropyridine (4)
2,6-Dimethyl-3,5-di-(2'-carbochloro-benzyloxy)-1,4-dihydropyridine (5)
2,6-Dimethyl-3,5-di-(2'-carbomethyl-benzyloxy)-1,4-dihydropyridine (6)
2,6-Dimethyl-3,5-di-(4'carbochloro-benzyloxy)-1,4-dihydropyridine (7)
2,6-Dimethyl-3,5-dicarbomethoxy-4-hexyl-1,4-dihydropyridine (8)
2,6-Dimethyl-3,5-dicarbomethoxy-4-propyl-1,4-dihydroyridine (9)
2,4,6-Trimethyl-3,5-dicarbophenoxy-1,4-dihydropyridine (10)
2,4,6-Trimethyl-3,5-di-(4'carbomethylphenoxy)-1,4-dihydropyridine (11)
2,4,6-Trimethyl-3,5-dicarbobenzyloxy-1,4-dihydropyridine (12)
2,4,6-Trimethyl-3,5-dicarboallyloxy-1,4-dihydropyridine (13)
2,4,6-Trimethyl-3,5-di-(4'carbochloro-benzoyloxy)-1,4-dihydropyridine (14)
2,6-Dimethyl-3,5-dicarbomethoxy-4-(1-pyropenyl)-1,4-dihydropyridine (15)
2,6-Dibenzyl-3,5-dicarbethoxy-1,4-dihydropyridine (16)
2,6-Di-(3-butenyl)-3,5-dicarbomethoxy-1,4-dihydropyridine (17)
2,6-Diphenyl-3,5-dicarbomethoxy-1,4-dihydropyridine (18)
2,6-Dimethyl-3,5-di-(2''-carbochloro-2'ethoxy-ethoxy)-1,4-dihydropyridine (19)
2,6-Ditridecyl-3,5-dicarbomethoxy-1,4-dihydropyridine (20)

As against this, the substance listed hereunder are already known but are considered as new stabilizers of polyvinyl chloride:
2,6-Dimethyl-3,5-dicarbobenzyloxy-1,4-dihydropyridine (21)
2,6-Dimethyl-3,5-dicarbocinnamyloxy-1,4-dihydropyridine (22)
2,6-Dimethyl-3,5-dicarbomethoxy-4-phenyl-1,4-dihydropyridine (23)
2,6-Diphenyl-3,5-dicarboethoxy-1,4-dihydropyridine (24)
2,6-Dimethyl-3,5-di-(2'-carbomethoxy-ethoxy)-1,4-dihydropyridine (25)
2,6-Dimethyl-3,5-di-(2'-carboethoxy-ethoxy)-1,4-dihydropyridine (26)
2,6-Dimethyl-3,5-di-(2'-carbobutoxy-ethoxy)-1,4-dihydropyridine (27)
2,6-Dimethyl-3,5-di-(2'-carbophenoxy-ethoxy)-1,4-dihydropyridine (28)
2,4,6-Trimethyl-3,5-dicarbomethoxy-1,4-dihydropyridine (29)

The invention also relates to the process of preparation of the compounds of formula I.

The compounds of the invention may be prepared according to the HANTZSCH synthesis, described in Chemical Reviews 72, I, 1972, by reacting a compound of the general formula:

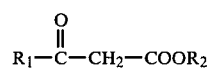

II wherein $R_1$ and $R_2$ have the same meanings as in formula I, with an aldehyde of the general formula:

III wherein $R_3$ has the same meanings as in formula I and with ammonia.

The compounds of formula II, wherein $R_1$ represents a methyl radical, can be prepared by one or the other of the following methods:

(1) By reacting a compound of the formula

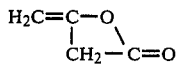

with an alcohol of the general formula:

$R_2OM$  IV wherein $R_2$ has the same meanings as in formula I, as described in Journal of Chemical Society, 854–60, 1954 and in Organic Synthesis 42, 28, 1962;

(2) By transesterifying in a known manner methyl acetoacetate of the formula

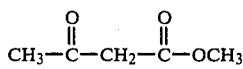

by means of an alcohol of the above formula IV.

The compounds of general formula II, wherein $R_1$ represents an alkyl chain containing from 2 to 16 carbon atoms may be prepared by reacting a halogenated derivative of the general formula:

$R_5X$  V wherein $R_5$ has the same meanings as $R_1$ as defined above but having one carbon atom less, with a compound of formula II wherein $R_1$ represents a methyl group, as described in Journal of American Chemical Society 4, 6702–6704, 1970 and in Bulletin de la Societe Chimique de France, 945–51, 1964.

Vinyl resins are known to deteriorate under the influence of heat and it is necessary to add a stabilizing agent to these masses of synthetic materials in order to retard thermodegradation and thus delay coloration of the resin.

Vinyl resins are also known to deteriorate under the influence of sunlight and a change in the original coloration may result therefrom.

This problem is particularly important where containers for food and drink are concerned. It is readily appreciated that food and drink could not be packed in containers of which the coloration may change in course of time.

The problem is the same with regard to floor-coverings, of which the coloration must also remain stable for a long period of time.

That is why stabilizers which are both thermostabilizers and photostabilizers are specially recommanded for vinyl resins.

Amongst the organic stabilizers there are already known the 1,4-butanediol-bis amino crotonate, the methyl aminocrotonate and the aminocrotonate of alcohols containing from 16 to 18 carbon atoms, compounds which have been described in "Les Matieres Plastiques dans l'Industrie Alimentaire" by R. LEFAUX, C.F.E. Paris (1972).

2-Phenyl-indole, however, is especially valuable due both to its good stabilizing power and to its low toxicity. It is, moreover, widely used in the plastic industry to stabilize vinyl polymers and co-polymers, especially those which are to be used for containing food and drink.

The compounds of the invention have many advantages over the aminocrotonates hereabove mentioned and also over 2-phenyl-indole.

For instance, the compounds of the invention already show a good stabilizing power when they are introduced into a vinyl resin in the proportion of 0.01 to 0.2 part per hundred parts in resin (p.h.p.r.), whereas the aminocrotonates and 2-phenyl-indole are to be used in a minimum proportion of 0.2 p.h.p.r. Moreover, the compounds of the invention are also superior to 2-phenyl-indole when used in a proportion of 0.2 to 1 p.h.p.r. This means that the stabilizers according to the invention can be used in lower proportions than well-known stabilizers.

This possibility of using lower proportions of stabilizers is a definite asset as far as plastic containers for food and drink are concerned. Besides the lower cost-price obtained, it should be remembered that when the concentration in stabilizer is lower, the amount of stabilizer extracted by the food or drink will also be lower.

Moreover, the compounds of the invention present a photostabilizing power which is far from negligible resulting in a better resistance of the resin to sunlight, i.e. in a reduced tendency to darken.

In addition, in resins requiring the use of a dye, which is very frequent in bottles for mineral water, the dihydroyridines according to the invention improve the basic colour and markedly increase the stability of the coloration.

Finally, the dihydropyridines of the invention possess valuable antioxidant properties, which are superior to those of the phenols, which are the most widely used antioxidants in vinyl resins (for instance, 2,6-diterbutyl-4-methyl-phenol).

When compared more particularly, to 2-phenyl-indole, the dihydropyridines according to the invention also present the following advantages:

Better transparency of the resin;

The colorations which are obtained do not affect the transparency of the resin and are perfectly stable;

Absence of yellowish tinges which are very common in vinyl resins.

This enables the use of blue-tinting agents to be avoided;

When the dihydropyridines of the invention are used as secondary stabilizers in resins containing as primary stabilizers calcium and calcium-zinc salts, they enable, when compared to 2-phenyl-indole used under the same conditions, the content of zinc in the resin to be diminished without affecting the thermostability of the latter. This is important since it is known that too much zinc causes defects in resin;

When the compounds of the invention are used as secondary stabilizers in a plastified resin, i.e. a resin containing as primary stabilizers barium-cadmium and calcium-zinc salts, they enable the content in cadmium, a very expensive and very toxic product, to be diminished while improving appreciably the basic colour and increasing thermostability.

Amongst the compounds of the invention, the stabilizers listed hereunder have been found to be particularly valuable:

2,6-Dimethyl-3,5-dicarboallyloxy-1,4-dihydropyridine (1)

2,6-Dimethyl-3,5-dicarboproparglloxy-1,4-dihydropyridine (2)

2,6-Dimethyl-3,5-dicarbobenzyloxy-1,4-dihydropyridine (21)

2,4,6-Trimethyl-3,5-dicarbomethoxy-1,4-dihydropyridine (29)

The stabilizers of formula I are incorporated in vinyl resins in a proportion of 0.01 to 1 p.h.p.r and preferably of 0.01 to 0.5 p.h.p.r.

The toxicity of the stabilizers of the invention was studied first and the satisfactory results obtained were such as to justify continuation of the investigation.

A. Acute toxicity

The acute toxicity of the stabilizers of the invention was measured by determining the dose of substance which provoked the death of 50% of the treated animals ($LD_{50}$).

A $LD_{50}$ superior to 2 g/kg was found in both mice and rats, no toxic symptoms being observed after 15 days.

B. Study of thermostabilizing power

The study of the thermostabilizing power of the compounds of the invention was extremely thorough.

It covers several phases, each of which is important from the point of view of the use of these stabilizers.

(1) Static thermostability

This study was carried out according to the GARDNER method, described in British Pat. No. 1,489,685.

The reference substance was 2-phenyl-indole, a well-known and widely used stabilizer.

The stabilizer (dihydropyridine or 2-phenyl-indole) and the other usual ingredients were mixed with powdered vinyl resins and the mixtures were calendered at a temperature of 160° C. to give rigid sheets.

The sheets were then heated in a thermostated oven (185° C. or 210° C.) for different intervals of time until incipient carbonization.

The coloration of the samples was compared to a standard scale of coloration, known as the GARDNER scale and was expressed in terms of the reference figures of the GARDNER scale.

This study was carried out with the following resin:

| Ingredients | Parts by weight |
| --- | --- |
| Polyvinyl chloride resin | 100 |
| Anti-shock resin | 9 |
| Epoxide soja bean oil | 2 |
| Calcium-12-Hydroxy-stearate | 0.2 |
| SL 2016 | 0.1 |
| Stabilizer | 0.3 or $1.55 \cdot 10^{-3}$ mol |

SL 2016 is a solution of zinc-2-ethyl-hexanoate in a mixture of hydrocarbons boiling between 158° C. and 184° C.

The first trial was carried out at 210° C. with a resin containing 0.3 part by weight of stabilizer, the sheets being removed from the oven every three minutes over a period of 21 minutes.

The following results were obtained:

| Stabilizer | 0 | 3 | 6 | 9 | 12 | 15 | 18 | 21 |
| --- | --- | --- | --- | --- | --- | --- | --- | --- |
| 1 | 1 | 1 | 2 | 4 | 7 | Burnt | | |
| 21 | 1 | 1 | 2 | 3 | 5.5 | 14 | Burnt | |
| 2-Phenyl-indole | 1 | 2 | 2 | 10 | 11 | 16 | Burnt | |
| 4 | 1 | 1 | 2 | 4 | 6 | 11 | Burnt | |
| 23 | 1 | 2 | 3 | 13 | 14 | 15 | Burnt | |
| 29 | 1 | 2 | 3 | 6 | 7 | 10 | 10.5 | Burnt |
| 8 | 1 | 2 | 3 | 6 | 8 | 10.5 | 11 | Burnt |
| 2-Phenyl-indole | 1 | 2 | 3.5 | 10.5 | 13 | 14 | Burnt | |
| 6 | 1 | 1 | 1.5 | 3 | 4 | 7 | Burnt | |
| 2-Phenyl-indole | 1 | 1 | 3 | 8 | 13 | 13 | Burnt | |
| 5 | 1 | 1 | 2 | 3 | 6 | 10.5 | Burnt | |
| 2-Phenyl-indole | 1 | 3 | 3 | 4 | 11 | 13 | Burnt | |
| 22 | 1 | 1 | 2 | 4 | 11 | Burnt | | |
| 2-Phenyl-indole | 1 | 2 | 2 | 9 | 11 | Burnt | | |
| 3 | 1 | 1 | 3 | 4 | 5 | 10.5 | Burnt | |
| 2-Phenyl-indole | 1 | 1 | 3 | 5 | 10.5 | 11 | Burnt | |
| 2 | 1 | 1 | 1 | 4 | 8 | 12 | Burnt | |
| 2-Phenyl-indole | 1 | 2 | 3 | 11 | 14 | 18 | Burnt | |
| 7 | 1 | 1 | 2 | 4 | 10.5 | 14 | Burnt | |
| 2-Phenyl-indole | 1 | 1 | 2 | 6 | 14 | 14 | Burnt | |
| 17 | 1 | 1 | 2 | 8 | 9 | Burnt | | |
| 2-Phenyl-indole | 1 | 1 | 2 | 11 | 13 | 16 | Burnt | |
| 16 | 1 | 1 | 3 | 4 | 11 | 18 | Burnt | |
| 2-Phenyl-indole | 1 | 1 | 3 | 9 | 14 | 18 | Burnt | |
| 25 | 1 | 1 | 1 | 1 | 1 | 4 | 11 | 17 |
| 2-Phenyl-indole | 1 | 2 | 2.5 | 2.5 | 10 | 13 | 16 | Burnt |
| 26 | 1 | 1 | 1 | 1 | 1.5 | 3 | 11 | Burnt |
| 18 | 1 | 1 | 2 | 2 | 2 | 3 | 6 | Burnt |
| 20 | 1 | 1 | 1.5 | 2 | 2 | 2.5 | 4 | 7 |
| 2-Phenyl-indole | 1 | 1 | 1 | 2 | 2 | 4 | 10.5 | 11 |
| 19 | 1 | 1 | 1 | 2 | 3 | 10 | 13 | Burnt |
| 2-Phenyl-indole | 1 | 1 | 1 | 2 | 4 | 11 | 13 | Burnt |
| 27 | 1 | 1 | 1 | 2 | 5 | 14 | Burnt | |
| 2-Phenyl-indole | 1 | 1 | 2 | 3 | 5 | 14 | 17 | Burnt |
| 28 | 1 | 1 | 1 | 3 | 4 | 5 | 10 | Burnt |
| 2-Phenyl-indole | 1 | 1 | 1 | 3 | 6 | 11 | 13 | Burnt |

The above results show a marked superiority of the thermostabilizing power of the dihydropyridines over 2-phenyl-indole, at least up to 12 minutes.

The coloration of the resins stabilized with compounds 1, 2, 4, 5 and 21 is considerably less over the period from 0 to 3 minutes.

Compounds 1, 2, 3, 16 and 17 have proved to be greatly superior to 2-phenyl-indole.

A second trial was performed at a temperature of 185° C., with a resin containing 0.3 part of stabilizer, the samples being removed from the oven every 6 minutes over a period of 24 minutes, then every 3 minutes until the 42nd minute (or until carbonization).

The results given hereunder were obtained:

| Stabilizer | Time in minutes | | | | | | | | | | |
|---|---|---|---|---|---|---|---|---|---|---|---|
| | 0 | 6 | 12 | 18 | 24 | 27 | 30 | 33 | 36 | 39 | 42 |
| 21 | 1 | 1 | 2 | 10 | 12 | 12 | 13 | 14 | Burnt | | |
| 4 | 1 | 1 | 2 | 8 | 13 | 14 | 17 | 18 | Burnt | | |
| 5 | 1 | 1 | 2 | 9 | 11 | 11 | 13 | 14 | 14 | Burnt | |
| 6 | 1 | 1 | 2 | 9 | 11 | 11 | 13 | 14 | Burnt | | |
| 2-Phenyl-indole | 1 | 1 | 3 | 5 | 13 | 14 | 15 | 15 | 16 | 16 | Burnt |
| 1 | 1 | 1 | 3 | 3 | 5 | 7 | 10 | 10.5 | 11 | 16 | Burnt |
| 2 | 1 | 1 | 2 | 4 | 6 | 7 | 8.5 | 9 | 10.5 | 12 | 18 |
| 2-Phenyl-indole | 1 | 1 | 4 | 9 | 13 | 14 | 14 | 14 | 14 | 15 | 15 |
| 3 | 1 | 1 | 5 | 8 | 10 | 10.5 | 13 | 14 | 18 | 18 | Burnt |
| 2-Phenyl-indole | 1 | 1 | 5 | 10.5 | 11 | 13 | 14 | 14 | 15 | 16 | 18 |

The above results taken as a whole show the superiority of the dihydropyridines over 2-phenyl indole during 30 minutes.

Finally, a trail was performed at 185° C., with resins containing equimolecular quantities of the dihydropyridines or of 2-phenyl-indole, namely $1.55 \times 10^{-3}$ mol. In this case too, the samples were removed from the oven every 6 minutes over a period of 24 minutes and then every 3 minutes until the 42nd minute (or until carbonization).

The following results were obtained:

| Stabilizer | Time in minutes | | | | | | | | | | |
|---|---|---|---|---|---|---|---|---|---|---|---|
| | 0 | 6 | 12 | 18 | 24 | 27 | 30 | 33 | 36 | 39 | 42 |
| 21 | 1 | 1 | 1 | 4 | 6 | 8 | 11 | 15 | Burnt | | |
| 4 | 1 | 1 | 1 | 4 | 6 | 8 | 11 | 15 | Burnt | | |
| 5 | 1 | 1 | 1 | 5 | 10 | 11 | 13 | 14 | 15 | Burnt | |
| 6 | 1 | 1 | 2 | 4 | 10 | 13 | B. | | | | |
| 2-Phenyl-indole | 1 | 2 | 3 | 10 | 13 | 14 | 14 | 14 | 16 | 16 | Burnt |

The dihydropyridines, when used in an equimolecular quantity to 2-phenyl-indole, show up to the 30th minute a thermostabilizing power superior to that of this latter compound.

(2) Study of the duration of thermostabilization

This study was carried out with vinyl resins which are used for manufacturing bottles for mineral water, namely resins containing calcium and zinc stearates, epoxy soja bean oil and either 2-phenyl-indole or a dihydropyridine of the invention (compound 1).

The following trials were carried out with various resins:

(1) The resin was mixed in a cylinder-mixer and the following parameters were measured:

The stability of the colour, i.e. the time which elapsed between the start of the mixing and the first visible change in the colour of the resin.

The thermostability, i.e. the time which elapsed between the start of the mixing and the carbonization of the resin.

With a resin containing 0.2% of stabilizer, it was found, after mixing at 220° C., that the resin containing 2-phenyl-indole as stabilizer changed colour after 3 minutes and carbonized after 13 minutes, whereas the resin containing 2,6-dimethyl-3,5-dicarboallyloxy-1,4-dihydropyridine (Compound 1) changed colour after five minutes and carbonized after 13.3 minutes.

(2) Examination of the colour of the resin after each passage (3 in all) in a blower-extruder, the mould being a 250 ml cylindrical flask.

Four resins where tested, the first containing 0.2% of 2-phenyl-indole and the others 0.2%, 0.03% and 0.015% of compound 1 respectively.

After the first passage the flask presented, with all four resins, a brilliant sky-blue colour.

After the second passage, the flask made with the resin containing 2-phenyl-indole presented a blue color tending towards green, whereas the other three flasks had kept the same colour.

After the third passage, the flask corresponding to the resin stabilized with 2-phenyl-indole had become greenish-blue, whereas the other three flasks still had the same brilliant sky-blue colour.

Two conclusions may be drawn from the above findings:

In equal concentrations, Compound 1 provides vinyl resin with a stability of colour which is markedly superior to that obtained with 2-phenyl-indole.

At a concentration of 0.015%, Compound 1 is at all times superior to 2-phenyl-indole used at a concentration of 0.2%.

Trials were also carried out with resins containing a larger quantity of zinc stearate.

The various proportions of calcium and zinc stearate and of the stabilizes are given in the following table:

| Additive | Quantity of stabilizer | | | | | | | | |
|---|---|---|---|---|---|---|---|---|---|
| N° of the resin | 1 | 2 | 3 | 4 | 5 | 6 | 7 | 8 | 9 |
| Calcium stearate | 0.29 | 0.29 | 0.29 | 0.29 | 0.29 | 0.29 | 0.29 | 0.29 | 0.15 |
| Zinc stearate | 0.32 | 0.32 | 0.32 | 0.32 | 0.32 | 0.32 | 0.15 | — | 0.32 |
| 2-Phenyl-indole | 0.15 | — | — | — | — | — | — | — | — |

| Additive | Quantity of stabilizer | | | | | | | | |
|---|---|---|---|---|---|---|---|---|---|
| N° of the resin | 1 | 2 | 3 | 4 | 5 | 6 | 7 | 8 | 9 |
| Compound 1 | — | 0.15 | 0.075 | 0.05 | 0.03 | 0.015 | 0.15 | 0.15 | 0.075 |

The same trials as hereabove were carried out and the following results were obtained (mixing at 220° C.)

| Trial | Resin | | | | | | | | |
|---|---|---|---|---|---|---|---|---|---|
| | 1 | 2 | 3 | 4 | 5 | 6 | 7 | 8 | 9 |
| Stability of the colour in min. | 2 to 3 | 5 | 4 | 4 | 3 | 3 | 3 | <1 | 3 |
| Thermostability in min. | 9 | 8.5 | 8 | 8 | 8 | 8 | 15 | <7 | 5 |

The results show that the improvement of the stability of the colour with compound 1 is very good, this latter compound being 10 to 15 times more effective than 2-phenyl-indole.

Compound 1 does not directly influence thermostability but it enables, by preserving the colour, the amount of zinc stearate to be reduced and also thermostability to be increased.

Examination of the colour of the resin after each passage through the blower-extruder, clearly showed the excellent behaviour of the resins containing compound 1.

(3) Study of the stabilization of plastified vinyl resins

This study was carried out by pressing plates from sheets which had been mixed for 5 minutes at 180° C., the pressing also lasting 5 minutes but at 170° C.

The same parameters as hereabove were studied, namely the duration of the stability of the colour, the duration of the thermostability and the colour of the pressed plate.

The following resins were used:

| Ingredients | Parts by weight | | | | | | | | |
|---|---|---|---|---|---|---|---|---|---|
| N° of the resin | 1 | 2 | 3 | 4 | 5 | 6 | 7 | 8 | 9 |
| Polyvinyl chloride resin | 100 | 100 | 100 | 100 | 100 | 100 | 100 | 100 | 100 |
| Wax E | 0.3 | 0.3 | 0.3 | 0.3 | 0.3 | 0.3 | 0.3 | 0.3 | 0.3 |
| Dioctylic Phthalate | 50 | 50 | 50 | 50 | 50 | 50 | 50 | 50 | 50 |
| Barium stearate | — | 0.375 | — | 0.375 | 0.375 | 0.375 | 0.375 | 0.375 | 0.375 |
| Cadmium stearate | — | — | 0.375 | 0.375 | 0.375 | 0.15 | 0.15 | 0.05 | 0.05 |
| Compound 1 | — | — | — | — | 0.1 | — | 0.05 | — | 0.05 |

The following results were obtained:

| Trial | N° of the resin | | | | | | | | |
|---|---|---|---|---|---|---|---|---|---|
| | 1 | 2 | 3 | 4 | 5 | 6 | 7 | 8 | 9 |
| Stability of the colour in min. | <5 | <5 | 25 | 35 | 50 | 30 | 45 | 20 | 35 |
| Thermostability in min. | <5 | 5 | 25 | 35 | 50 | 30 | 55 | 25 | 50 |

It can be noted that Compound 1 has a favourable influence on the stability of the plate in plastified resin since it:

increases the time elapsing between the start of the treatment and the first visible change of colour;

increases the time elapsing between the start of the treatment and the carbonization of the resin.

Examination of the colour of the various resins shows that the addition of Compound 1 has a favourable influence on the basic colour, this latter approaching the colourless.

(4) Study of the stabilization of vinyl co-polymers

The study of the static thermostability of vinyl co-polymers was carried out according to the GARDNER method described above and, also in a more detailed manner in British Patent No. 1,489,685.

(a) Rigid co-polymer vinyl chloride-vinyl acetate
The following compound was prepared:

| Ingredient | Parts by weight |
|---|---|
| Co-polymer vinyl chloride-vinyl acetate | 80 |
| Vinyl chloride resin | 20 |
| Calcium stearate | 0.5 |
| Stabilizer | 0 or 0.1 |

The sheets were heated in a ventilated oven at 185° C. and the following results were obtained:

| Stabilizer | Time in min. | | | | | | | |
|---|---|---|---|---|---|---|---|---|
| | 0 | 2 | 4 | 6 | 8 | 10 | 12 | 14 |
| None | 1.5 | 2 | 4 | 11.5 | 15 | 17 | 18 | 18.5 |
| 28 | 1 | 1 | 4 | 10 | 12 | 13 | 15 | 17 |

The above results clearly show the thermostabilizing properties of Compound 28.

(b) Flexible co-polymer vinyl chloride-vinyl acetate.
The following compound was prepared:

| Ingredient | Parts by weight |
|---|---|
| Co-polymer vinyl chloride-vinyl acetate | 100 |
| Dioctylic phthalate | 60 |
| Melamine | 2 |
| Calcium stearate | 2 |
| Stabilizer | 0 or 0.2 |

The resin was allowed to gel for 5 minutes at 120° C. and the sheets were heated at 160° C. in a Metrastat oven. The following results were obtained:

| Stabilizer | Time in min. | | | | |
|---|---|---|---|---|---|
| | 0 | 30 | 40 | 50 | 60 |
| None | 1 | 6 | 13 | 14 | 17 |
| 28 | 1 | 2 | 6 | 12 | 15 |
| 21 | 1 | 1 | 3 | 8 | 15 |

-continued

| Stabilizer | Time in min. | | | | |
|---|---|---|---|---|---|
| | 0 | 30 | 40 | 50 | 60 |
| 1 | 1 | 2 | 6 | 12 | 15 |

(c) Flexible co-polymer vinyl chloride-vinyl acetate
The following compound was prepared:

| Ingredient | Parts by weight |
|---|---|
| Co-polymer vinyl chloride-vinyl acetate | 100 |
| Dioctylic phthalate | 40 |
| Calcium stearate | 2 |
| Melamine | 2 |
| Stabilizer | 0 or 0.3 |

The sheets were heated in a Metrastat oven at 160° C. and the following results were obtained:

| Stabilizer | Time in min. | | | | | | |
|---|---|---|---|---|---|---|---|
| | 0 | 10 | 20 | 30 | 40 | 50 | 60 |
| None | 1 | 1 | 5 | 8 | 12 | 13 | 13 |
| 28 | 1 | 1 | 2 | 5 | 7 | 10 | 12 |
| 21 | 1 | 1 | 2 | 5 | 6 | 7 | 12 |
| 1 | 1 | 1 | 2 | 4 | 5.5 | 6 | 7 |

(d) Rigid co-polymer vinyl chloride-vinylidene chloride
The following compound was prepared:

| Ingredient | Parts by weight |
|---|---|
| Vinyl chloride resin | 90 |
| Co-polymer vinyl chloride-vinylidene chloride | 10 |
| Anti-shock agent | 8 |
| Epoxide soja bean oil | 4 |
| Calcium stearate | 0.2 |
| Zinc stearate | 0.1 |
| Hydrogenated rape-seed oil | 1.2 |
| Glyceryl trimontanate | 0.4 |
| Stabilizer | 0 or 0.3 |

The sheets were heated in a ventilated oven at 210° C. The following results were obtained:

| Stabilizer | Time in min. | | | | | |
|---|---|---|---|---|---|---|
| | 0 | 3 | 6 | 9 | 12 | 15 |
| none | 2 | 2 | 5 | 10.5 | 14 | 16 |
| 21 | 1.5 | 2 | 2 | 3 | 7 | 15 |
| 28 | 1.5 | 2 | 3 | 3.5 | 7 | 15 |

(e) Rigid co-polymer vinyl chloride-vinylidene chloride
The following compound was prepared:

| Ingredient | Parts by weight |
|---|---|
| Vinyl chloride resin | 90 |
| Vinyl chloride-vinylidene chloride co-polymer | 10 |
| Anti-shock agent | 8 |
| Epoxide soja bean oil | 4 |
| Calcium stearate | 0.2 |
| Zinc stearate | 0.1 |
| Hydrogenated rape-seed oil | 1.2 |
| Glyceryl trimontanate | 0.4 |
| Stabilizer | 0 or 0.3 |

The sheets were heated in a ventilated oven at 210° C. and the following results were obtained:

| Stabilizer | Time in min. | | | | |
|---|---|---|---|---|---|
| | 0 | 3 | 6 | 9 | 12 |
| None | 1.5 | 2.5 | 4.5 | 11 | 14 |
| 1 | 1 | 1 | 2 | 4 | 10 |

It is clear from tests b, c, d and e that the compounds of the invention have a marked stabilizing action on vinyl chloride co-polymers.

(5) Comparison of the compounds of the invention with β-aminocrotonate derivatives.

(a) Comparison with 1,4-butanediol-β-aminocrotonate and with methyl-β-aminocrotonate.
The following rigid co-polymer was prepared:

| Ingredients | Parts by weight |
|---|---|
| Co-polymer vinyl chloride-vinyl acetate containing 15% of acetate | 80 |
| Vinyl chloride polymer | 20 |
| Calcium stearate | 0.5 |
| Stabilizer | 0.5 |

The sheets were heated in a ventilated oven at 185° C. and the following results were obtained:

| Stabilizer | Time in min. | | | | | | |
|---|---|---|---|---|---|---|---|
| | 0 | 2 | 4 | 6 | 8 | 10 | 12 |
| 1,4-butanediol-β-aminocrotonate | 1 | 1 | 4 | 10 | 13 | 15 | 18 |
| Methyl-β-aminocrotonate | 1 | 1 | 5 | 12 | 14 | 17 | 18 |
| Compound 21 | 1 | 1 | 4 | 6 | 11 | 13 | 17 |
| Compound 28 | 1 | 1 | 5 | 7 | 11 | 13 | 17 |

(b) Comparison with stabilizer G1
Stabilizer G1 is a mixture of 1,4-butanediol-β-aminocrotonate and of β-aminocrotonate of alcohols containing from 16 to 18 carbon atoms.
The following rigid co-polymer was prepared:

| Ingredients | Parts by weight |
|---|---|
| Co-polymer vinyl chloride-vinyl acetate containing 15% of acetate | 80 |
| Vinyl chloride polymer | 20 |
| Calcium stearate | 0.5 |
| Stabilizer | 0.5 |

The sheets were heated in a ventilated oven at 185° C. and the following results were obtained:

| Stabilizer | Time in min. | | | | | | |
|---|---|---|---|---|---|---|---|
| | 0 | 2 | 4 | 6 | 8 | 10 | 12 |
| G 1 | 1 | 1 | 4 | 11 | 12.5 | 16 | 18.5 |
| 2 | 1 | 1 | 1.5 | 5 | 10 | 12 | 16 |
| 1 | 1 | 1 | 2 | 6 | 10 | 13 | 17 |
| G 1 | 1 | 1 | 2.5 | 11 | 13.5 | 17 | 18.5 |
| 27 | 1 | 1 | 4 | 7 | 12.5 | 17 | — |

Another comparison was made with the following rigid co-polymer:

| Ingredients | Parts by weight |
| --- | --- |
| Co-polymer vinyl chloride-vinyl acetate containing from 12.5 to 13.5% of acetate | 100 |
| Glyceryl tribehenate | 0.4 |
| Calcium stearate | 0.5 |
| Stabilizer | 0.5 |

The sheets were heated in a ventilated oven at 185° C. and the following results were obtained:

| Stabilizer | Time in min. | | | | | | | |
| --- | --- | --- | --- | --- | --- | --- | --- | --- |
| | 0 | 2 | 4 | 6 | | 10 | 12 | 14 |
| G 1 | 1 | 2 | 3 | 4 | | 9 | 12 | 18 | — |
| 2 | 1 | 1 | 2 | 3 | | 4 | 8.5 | 13 | 17 |
| 1 | 1 | 1 | 2 | 3 | | 7 | 12 | 18 | — |

A test was also carried out with the following compound:

| Ingredients | Parts by weight |
| --- | --- |
| Co-polymer vinyl chloride-vinyl acetate containing 15% of acetate | 80 |
| Vinyl chloride resin | 20 |
| Calcium stearate | 0.5 |
| Stabilizer | 0.3 |

The sheets were heated in a ventilated oven at 185° C. and the following results were obtained:

| Stabilizer | Time in min. | | | | | | | |
| --- | --- | --- | --- | --- | --- | --- | --- | --- |
| | 0 | 2 | 4 | 6 | 8 | 10 | 12 | 14 |
| G 1 | 1 | 1 | 2 | 3 | 6 | 10 | 12.5 | 16 |
| 28 | 1 | 1 | 2 | 4 | 5 | 9 | 11 | 13 |
| G 1 | 1 | 1 | 2 | 6 | 11.5 | 16 | 18 | Burnt |
| 21 | 1 | 1 | 2 | 4 | 7 | 12 | 16 | 18 |

Another test was made with the same resin but containing 0.1 part of stabilizer.

The sheets were also heated in a ventilated oven at 185° C. and the following results were obtained:

| Stabilizer | Time in min. | | | | | | | |
| --- | --- | --- | --- | --- | --- | --- | --- | --- |
| | 0 | 2 | 4 | 6 | 8 | 10 | 12 | 14 |
| G 1 | 1 | 1 | 6 | 7 | 11 | 12 | 14 | 16 |
| 2 | 1 | 1 | 2 | 4 | 8 | 10 | 12 | 13 |
| 1 | 1 | 1 | 2 | 4 | 8 | 11 | 12 | 13 |
| G 1 | 1 | 1 | 2 | 6 | 13 | 16 | 18 | — |
| 21 | 1 | 1 | 2 | 4 | 11 | 13 | 17 | — |

(c) Comparison with 2-phenyl-indole

A comparative test was made using the following compound:

| Ingredients | Parts by weight |
| --- | --- |
| Co-polymer vinyl chloride-vinyl acetate containing 15% of acetate | 80 |
| Vinyl chloride resin | 20 |
| Calcium stearate | 0.5 |
| Stabilizer | 0.3 |

The sheets were heated in a ventilated oven at 185° C. and the following results were obtained:

| Stabilizer | Time in min. | | | | | | | |
| --- | --- | --- | --- | --- | --- | --- | --- | --- |
| | 0 | 2 | 4 | 6 | 8 | 10 | 12 | 14 |
| 2-phenyl-indole | 1 | 1 | 2 | 3 | 8 | 12 | 14 | 17 |
| 21 | 1 | 1 | 2 | 3 | 7 | 10 | 12 | 16 |

A second test was made using the following compound:

| Ingredients | Parts by weight |
| --- | --- |
| Vinyl chloride resin | 90 |
| Co-polymer vinyl chloride-vinylidene chloride containing 70% of vinylidene chloride | 10 |
| Antishock agent | 8 |
| Epoxide soja bean oil | 4 |
| Calcium stearate | 0.2 |
| Zinc stearate | 0.1 |
| Hydrogenated rape-seed oil | 1.2 |
| Glyceryl trimontanate | 0.4 |
| Stabilizer | 0.3 |

The sheets were heated in a ventilated oven at 210° C. and the following results were obtained:

| Stabilizer | Time in min. | | | | | |
| --- | --- | --- | --- | --- | --- | --- |
| | 0 | 3 | 6 | 9 | 12 | 15 |
| 2-phenyl-indole | 2 | 2 | 5 | 8.5 | 14 | 16 |
| 21 | 1.5 | 2 | 2 | 3 | 7 | 15 |
| 28 | 1.5 | 2 | 3 | 3.5 | 7 | 15 |
| 2-phenyl-indole | 1 | 1 | 4 | 10 | 15 | — |
| 1 | 1 | 1 | 2 | 4 | 10 | — |

The above results clearly show that the dihydropyridines of the invention have a stabilizing action on vinyl co-polymers which is markedly superior to that of well-known stabilizers, such as the β-aminocrotonate derivatives and 2-phenyl-indole.

C. Study of photostabilizing power (1) Vinyl polymers

The photostabilizing power of the compounds of the invention was studied by exposing to the sun polyvinyl chloride plates which had been stabilized either by a dihydropyridine of the invention or by 2-phenyl-indole, or again by 2-(3'-methoxy-4'-hydroxy)-indole. This last product is an extremely valuable thermostabilizer for thermoplastic resins and is described in British Pat. No. 1,489,685.

The resin given hereunder was prepared by mixing on cylinders at 160° C.:

| Ingredients | Parts by weight |
| --- | --- |
| Polyvinyl chloride resin | 100 |
| Anti-shock resin | 8 |
| Epoxide soja bean oil | 4 |
| Acrylic resin | 0.5 |
| Trinonylphenyl phosphate | 0.3 |
| SL 2016 | 0.25 |
| Calcium behenate | 0.4 |
| Hydrogenated castor oil | 0.2 |
| Glyceryl trimontanate | 0.4 |
| Stabilizer | 0.3 |

The plates of stabilized polyvinyl chloride, together with a plate which had not been stabilized, were stood in the sun under the same conditions and at the same time. Their colour was measured after 6 hours and 12 hours of exposure.

The coloration of the plates was determined according to two methods:

On the plates themselves, following the GARDNER scale, as in the section on thermostability, On a solution of these plates in tetrahydrofuran, the coloration of th solution being measured according to the French Pharmacopeia (IXth edition, II-338).

The following results were obtained:

| Stabilizer | Coloration of the plates GARDNER Time of exposure to sun | | | Coloration of the plates FRENCH PHARMACOPEIA Time of exposure to sun | | |
|---|---|---|---|---|---|---|
| | 0 | 6h | 12h | 0 | 6h | 12h |
| Standard | 3+ | 3+ | 3+ | J5 | J5 | J5 |
| 2-(3'-Methoxy-4'-hydroxy-phenyl)-indole | 1 | 4 | 8 | B5 | B4 to JB4 | B3 to JB3 |
| 2-Phenyl-indole | 2⁻ | 3 | 5+ | J6 | J5 | J4 |
| Compound 1 | 1 | 1 | 1.5 | J6 | J5 | J5 |
| Compound 2 | 1 | 1 | 1.5 | JV6 | JV6 | JV5 |
| Compound 21 | 1 | 1 | 1.5 | JV6 | JV6 | JV5 |
| Compound 29 | 2⁻ | 3 | 5 | JV6 | JV5 | JV4 |

The sign + means that the coloration lies between the lower unit and the upper half-unit. Thus, 3+ means that the coloration lies between 3 and 3.5. Similarly, the sign − means that the coloration lies between the lower half-unit and the upper unit.

It may be concluded from the above results that the dihydropyridines according to the invention have a photostabilizing power on vinyl polymers which is markedly superior to that of 2-phenyl-indole and of its derivative.

(2) Vinyl co-polymers

The sheets were exposed to the sun and their colorations were also determined according to the GARDNER method.

(a) Co-polymer vinyl chloride-vinyl acetate
The following compound was prepared:

| Ingredients | Parts by weight |
|---|---|
| Co-polymer vinyl chloride-vinyl acetate containing 15% of acetate | 100 |
| Dioctylic phthalate | 40 |
| Calcium stearate | 2 |
| Melamine | 2 |
| Wax | 1 |
| Stabilizer | 0.3 |

The following results were obtained:

| Stabilizer | Time in hours Colour in GARDNER degrees | |
|---|---|---|
| | Time 0 | After 24 hours |
| 2-Phenyl-indole | 1 | 6 |
| 27 | 1 | 2 |
| 2-Phenyl-indole | 1 | 8 |
| 1 | 1 | 1 |
| 28 | 1 | 1 |
| 21 | 1 | 1 |

(b) Rgid co-polymer vinyl chloride-vinylidene chloride
The following compound was prepared:

| Ingredients | Parts by weight |
|---|---|
| Vinyl chloride resin | 90 |
| Co-polymer vinyl chloride-vinylidene chloride containing 70% of vinylidene chloride | 10 |
| Anti-shock agent | 8 |
| Epoxide soja bean oil | 4 |
| Calcium stearate | 0.2 |
| Zinc stearate | 0.1 |
| Hydrogenated rape-seed oil | 1.2 |
| Glyceryl trimontanate | 0.4 |
| Stabilizer | 0.3 |

The following results were obtained:

| Stabilizer | Time in hours Colour in GARDNER degrees | |
|---|---|---|
| | Time 0 | After 24 hours |
| 2-Phenyl-indole | 1.5 | 17 |
| 21 | 1.5 | 3.5 |
| 28 | 1.5 | 3.5 |
| 2-Phenyl-indole | 1 | 13 |
| 1 | 1 | 2 |

The above results clearly show the marked superiority of the compounds of the invention over 2-phenyl-indole with regard to the stablization of vinyl co-polymers.

D. Study of antioxidant power

The value of the antioxidant power of the 1,4-dihydropyridines of the invention was demonstrated by two differents methods:

By a polarographic study of their oxidation potential, compared to well-known antioxidants such as 2,6-diterbutyl-4-methyl-phenol, 2-terbutyl-4-methoxy-phenol, 4-methoxy-phenol and hydroquinone.

By direct comparison, on a polyvinyl chloride resin, of the antioxidant power of Compound 1 of the invention and that of an antioxidant known as one of the most valuable and frequently used in polyvinyl chloride, namely 2,6-diterbutyl-4-methyl-phenol.

(1) Polarographic study of the oxidation potential (a) Operating conditions

Electrodes

Reference electrode: Calomel electrode containing a saturated solution of anhydrous lithium perchlorate as bridge liquid.

Working electrode: Vitrous carbon rotating electrode (2,500 r.p.m.)

Counter-electrode: Platinum electrode

Chemical products

Acetonitrile containing less than 0.1% of water and presenting no polarographic waves between −2.5 V and +2.5 V.

Anhydrous lithium perchlorate containing less than 1% of water.

Reactant

A 0.1 M solution of lithium perchlorate in acetonitrile, treated and preserved on a 4 A molecular sieve.

Polarographic conditions

Tension: 10 mV
Initial potential: 0 V
Amplitude of exploration: 0 to 2 V
Speed of exploration: 10 mV/second
Sensitivity: 1.25 μA to 50 μA
Mean concentration: about $0.3 \times 10^{-3}$ mol/liter

Precautions

Between each measurement, the vitrous carbon electrode and the platinum electrode were carefully cleaned with Joseph paper.

Results

| Substance | Oxidation potential in volts |
|---|---|
| 1 | 0.75 ± 0.01 |
| 21 | 0.73 ± 0.01 |
| 2 | 0.80 ± 0.01 |
| 2,6-Diterbutyl-4-methyl-phenol | 1.11 ± 0.02 |
| 2-Terbutyl-4-methoxy-phenol | 0.81 ± 0.01 |
| Hydroquinone | 0.83 ± 0.01 |
| 4-Methoxy-phenol | 0.89 ± 0.01 |

The above results show that the dihydropyridines are more reducing than the substance usually used as antioxidants.

(2) Trial on a polyvinyl chloride resin

The antioxidant power of Compound 1 was compared to that of 2,6-diterbutyl-4-methyl-phenol (Compound 2) by using the following resin:

| Ingredients | Parts by weight |
|---|---|
| Polyvinyl chloride resin | 100 |
| Anti-shock agent | 10 |
| Acrylic resin | 0.5 |
| Epoxide soja bean oil | 3 |
| SL 2016 | 0.1 |
| Zinc and calcium stearates | 0.2 |
| Hydrogenated castor oil | 1.5 |
| Polyethylene wax | 0.3 |
| Antioxidant | from 0.05 to 1 |

The study was carried out according to the GARDNER method, the samples being removed from an oven at 185° C. every 10 minutes over a period of 80 minutes.

The following results were obtained:

| Concentration part per 100 parts | Antioxidant | \multicolumn{9}{c}{Time in minutes} | | | | | | | | |
|---|---|---|---|---|---|---|---|---|---|---|
| | | 0 | 10 | 20 | 30 | 40 | 50 | 60 | 70 | 80 |
| 0.05 | Compound Z | >1 | 1+ | 2− | 5+ | >6 | 7 | 7 | 8 | Burnt |
| | Compound 1 | 1 | 1 | 1+ | 3+ | 4− | 6+ | 7 | 8 | B |
| 0.1 | Compound Z | >1 | 1+ | 2− | >5 | >6 | 7 | 7 | 8 | B |
| | Compound 1 | 1 | 1 | 1+ | <2 | 3+ | 5+ | 7 | 7 | B |
| 0.2 | Compound Z | >1 | 1+ | 2+ | 5− | >6 | 7 | 7 | 8 | B |
| | Compound 1 | 1 | 1 | 1 | 1+ | 2 | 3 | 5 | >6 | B |
| 0.3 | Compound Z | <1+ | 1+ | >2 | 6 | 7 | 8 | 8 | 8+ | B |
| | Compound 1 | 1 | 1 | 1 | 1 | 2 | >2 | 8 | 8 | B |
| 0.4 | Compound Z | <1+ | >1+ | 3 | >6 | 8− | 9 | 9 | 9 | B |
| | Compound 1 | 1 | 1 | 1 | 1 | 1+ | >2+ | 4 | 8 | B |
| 0.5 | Compound Z | <1+ | >1+ | 3 | >6 | >7 | 8− | 8 | 8 | B |
| | Compound 1 | 1 | 1 | 1 | >1 | 1+ | >2+ | $4^{-8}$ | B | |
| 1.0 | Compound Z | 1+ | 2− | >3 | 8 | 8 | 8 | 9 | 9 | B |
| | Compound 1 | 1 | 1 | 1 | 1 | 1+ | 4 | 8 | B | |

The signs + and − have the same meanings as in the previous table and > 2 means that the coloration lies between 2 and 2+.

The following conclusions can be drawn from the above table: up to 50 minutes in the oven at 185° C., Compound 1 proved to be superior to Compound Z at every concentration.

Moreover, no concentration in Compound Z gives the best results obtained with Compound 1.

The same trials were carried out in a Metrastat oven at 210° C.

The following results were obtained:

| Concentration part per 100 parts | Antioxidant | \multicolumn{6}{c}{Time in minutes} | | | | | |
|---|---|---|---|---|---|---|---|
| | | 0 to 10 | 10 to 20 | 20 to 25 | 25 to 30 | 30 to 35 | 35 to 40 |
| 0.05 | Compound Z | 2− | 2 | 3− | 4+ | 10 | >10 B/38' |
| | Compound 1 | 1 | 1 | 1 | 1 | 5− | >10 B/40' |
| 0.1 | Compound Z | 2− | 2 | 3− | 4+ | 11 | >11 B/39' |
| | Compound 1 | 1 | 1 | 1 | 1 | 5− | <10 B/38' |
| 0.2 | Compound Z | 2− | 2 | 3− | 4+ | 11 | >11 B/39' |
| | Compound 1 | 1 | 1 | 1 | 1 | 5− | <9 B/39' |
| 0.3 | Compound Z | <1 | 2− | 3− | 3 | 9 | <10 B/39' |
| | Compound 1 | 1 | 1 | 1 | 1 | 3+ | <9 B/39' |
| 0.4 | Compound Z | 2− | 2 | 3 | 3+ | 10 | >10 B/38' |
| | Compound 1 | 1 | 1 | 1 | 1 | 4− | 6− B/38' |
| 0.5 | Compound Z | 2− | 2 | 3 | 3+ | 10+ | >10+ B/38' |
| | Compound 1 | 1 | 1 | 1 | 1 | 3+ | 6− |

-continued

| Concentration part per 100 parts | Anti-oxidant | Time in minutes | | | | | |
|---|---|---|---|---|---|---|---|
| | | 0 to 10 | 10 to 20 | 20 to 25 | 25 to 30 | 30 to 35 | 35 to 40 |
| 1.0 | Compound Z | 2⁻ | 2 | 3⁻ | 5 | 11 | 1 B/38' >11 B/38' |
| | Compound 1 | 1 | 1 | 1 | 1 | 2+ | 2+ B/37' |

As is the previous trial, Compound 1 was found to be markedly superior to Compound Z. Moreover, all the samples containing Compound Z gave, from the time zero, pink-coloured sheets, which is another disadvantage as compared to the dihydropyridine of the invention.

The following Examples provide a non-limitative illustration of the process of preparation of the compounds of the invention.

EXAMPLE 1

Preparation of 2,6-dimethyl-3,5-dicarboallyloxy-1,4-dihydropyridine

Into a reactor cooled in an ice-bath were introduced 28.4 g (0.2 mol) of allyl acetoacetate and 0.2 g of diethylamine.

The solution was cooled to 0° C. and 7.5 g (0.1 mol) of a 40% aqueous solution of formic aldehyde was introduced drop-by-drop in 90 minutes, care being taken to maintain the temperature below or equal to 10° C.

The reaction medium was maintained at 0° C. for 6 hours, and then at room-temperature for 40 hours.

The solution was decanted and the aqueous phase was extracted with ether. The ethereal phase was added to the oily phase and was dried over anhydrous sodium sulphate.

The solution was filtered, the ether eliminated and the oily residue diluted with one part of methanol.

Ammonia was bubbled through the solution obtained, the temperature being maintained at 0° C., and the solution saturated with ammonia was allowed to stand at room-temperature for 12 hours.

The solution was filtered on a Buchner funnel and the solid residue so obtained was recrystallized from acetone to give 2,6-dimethyl-3,5-dicarboallyloxy-1,4-dihydropyridine.

Yield: 75%.
Melting point: 167° C.

By the method described above but using the appropriate starting-products, the following compounds were prepared:

| Compound | Yield % | Melting point °C. |
|---|---|---|
| 2,6-Dimethyl-3,5-dicarbopropargyloxy-1,4-dihydropyridine | 60 | 202–203 (acetone) |
| 2,6-Dimethyl-3,5-di-(2'-carbochloroethoxy)-1,4-dihydropyridine | 31 | 158 (acetone) |
| 2,6-Dimethyl-3,5-di-(4'-carbomethoxybenzyloxy)-1,4-dihydropyridine | 18 | 143 (benzene 55° C.) |
| 2,6-Dimethyl-3,5-dicarbobenzyloxy-1,4-dihydropyridine | 57 | 122 (benzene) |
| 2,6-Dimethyl-3,5-dicarbocinnamyloxy-1,4-dihydropyridine | 37 | 156 |

-continued

| Compound | Yield % | Melting point °C. |
|---|---|---|
| | | (benzene then acetone) |
| 2,6-Dimethyl-3,5-di-(2'-carbochlorobenzyloxy)-1,4-dihydropyridine | 44 | 190 (acetone) |
| 2,6-Dimethyl-3,5-di-(2'-carbomethylbenzyloxy)-1,4-dihydropyririne | 47 | 149 (acetone) |

EXAMPLE 2

Preparation of 2,6-dimethyl-3,5-dicarbopropargyloxy-1,4-dihydropyridine

Into a reactor were introduced 14 g (0.1 mol) of propargyl acetoacetate, 10.5 g (0.075 mol) of tetramine hexamethylene, 2.9 g (0.038 mol) of ammonium acetate, 36 g of methanol and 5 g of water.

Under a light flow of nitrogen, the reaction medium was refluxed for one hour and was allowed to cool to room-temperature and was then poured into a mixture of water and ice.

The precipitate which formed was filtered off and was washed with hot acetone in order to eliminate the excess of tetramine hexamethylene.

The precipitate was dried to constant weight and washed with hot acetone to give 2,6-dimethyl-3,5-dicarbopropargyloxy-1,4-dihydropyridine.

Yield: 75%
Melting Point: 206° C.

By the above procedure but using the appropriate starting-product, the following compounds were prepared:

| Compound | Yield % | Melting Point °C. |
|---|---|---|
| 2,6-Dimethyl-3,5-dicarboallyloxy-1,4-dihydropyridine | 86 | 168 (washing with hot acetone) |
| 2,6-Dimethyl-3,5-di-(4'-carbochlorobenzyloxy)1,4-dihydropyridine | 82 | 171 (acetone) |
| 2,6-Dimethyl-3,5-dicarbobenzyloxy-1,4-dihydropyridine | 75 | 120 (methanol) |
| 2,6-Dimethyl-3,5-di-(2'-carbobutoxyethoxy)-1,4-dihydropyridine | 40 | 95 (methanol) |
| 2,6-Dimethyl-3,5-di-(2'-carbomethoxyethoxy)-1,4-dihydropyridine | 70 | 107 (methanol) |
| 2,6-Dimethyl-3,5-di-(2'-carboethoxyethoxy)-1,4-dihydropyridine | 65 | 109 (methanol then acetone) |
| 2,6-Dimethyl-3,5-di-(2'-carbophenoxyethoxy)-1,4-dihydropyridine | 55 | 132 (acetone) |
| 2,6-Diphenyl-3,5-dicarbethoxy-1,4-dihydropyridine | 10 | 142 (ethylic ether) |
| 2,6-Dibenzyl-3,5-dicarbethoxy-1,4-dihydropyridine | 51 | 118 (methanol) |
| 2,6-Di-3-butenyl-3,5-dicarbomethoxy-1,4-dihydropyridine | 46 | 79 (benzene/pentane 10/30) |

-continued

| Compound | Yield % | Melting Point °C. |
|---|---|---|
| 2,6-Dimethyl-3,5-di-(2''-carbochloro-2'-ethoxy-ethoxy)-1,4-dihydropyridine | 79 | 110 (methanol) |
| 2,6-Diphenylethyl-3,5-dicarbomethoxy-1,4-dihydropyridine | 59 | 156 (methanol-acetone 80/20) |
| 2,6-Ditridecyl-3,5-dicarbomethoxy-1,4-dihydropyridine | 73 | 61 (acetone) |

EXAMPLE 3

Preparation of 2,4,6-trimethyl-3,5-dicarbomethoxy-1,4-dihydropyridine

Into a reactor were introduced 232 g (2 mols) of methyl acetoacetate and 160 g of methanol. While stirring, 44 g (1 mol) of freshly distilled acetaldehyde were added drop-by-drop, at 15° C.

Temperature and stirring were maintained for 15 minutes under a light flow of nitrogen and 90 g of a 20% ammonium hydroxide solution (1.15 mol) were added at room-temperature. The temperature rose to 45° C. and the mixture was heated to the methanol reflux temperature for one hour.

After cooling, the reaction medium was poured into a water-ice mixture and the precipitate which formed was filtered off on a Buchner funnel.

The precipitate was thoroughly washed with water and was recrystallized from methanol to give 2,4,6-trimethyl-3,5-dicarbomethoxy-1,4-dihydropyridine.
Yield: 69%
Melting point: 155°–156° C.

By the above procedure but using the appropriate starting-product, the following compounds were prepared:

| Compound | Yield % | Melting Point °C. |
|---|---|---|
| 2,6-Dimethyl-3,5-dicarbomethoxy-4-hexyl-1,4-dihydropyridine | 70 | 100 (cyclohexane) |
| 2,6-Dimethyl-3,5-dicarbomethoxy-4-propyl-1,4-dihydropyridine | 57 | 140 (acetone) |
| 2,4,6-Trimethyl-3,5-di-(4'carbomethyl-phenoxy)-1,4-dihydropyridine | 20 | 192 (acetone) |
| 2,4,6-Trimethyl-3,5-dicarbobenzyloxy-1,4-dihydropyridine | 61 | 123 (methanol) |
| 2,4,6-Trimethyl-3,5-dicarboallyloxy-1,4-dihydropyridine | 55 | 100 (benzene-hexane) |
| 2,4,6-Trimethyl-3,5-di-(4'-carbochloro-benzyloxy)-1,4-dihydropyridine | 28 | 161 (methanol) |

EXAMPLE 4

Preparation of 2,6-dimethyl-3,5-dicarbomethoxy-4-(1-propenyl)-1,4-dihydropyridine Into a reactor were introduced at room-temperature 23.2 g (0.2 mol) of methyl acetoacetate and 7 g (0.1 mol) of crotonaldehyde. While stirring, a solution of 40 g (0.42 mol) of ammonium carbonate in 400 g of water was added and stirring was maintained for 20 hours at room-temperature.

The gummy precipitate was cooled by ether and the ethereal solution was washed with water, dried over sodium sulphate and the ether was evaporated off.

The crude product was recrystallized from a mixture of ethanol and hexane to give 2,6-dimethyl-3,5-dicarbomethoxy-4-(1-propenyl)-1,4-dihydropyridine.
Yield: 60%
Melting point: 176° C.

We claim:

1. Process for stabilizing a vinyl resin whereby a stabilizer of the following formula is introduced into a polymer or co-polymer of vinyl chloride:

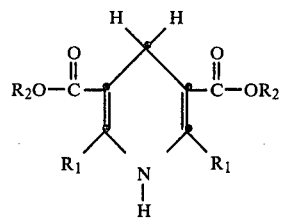

wherein $R_1$ represents methyl or phenyl and $R_2$ represents benzyl, o-methylbenzyl, p-methylbenzyl, 2-phenoxyethyl or cinnamyl.

2. Process according to claim 1 whereby the compound of formula I is introduced into the vinyl resin in a proportion of 0.01 to 1 part by 100 parts of resin by weight.

3. Process according to claim 1 whereby the compound of formula I is introduced into the vinyl resin in a proportion of 0.01 to 0.5 part by 100 parts of resin by weight.

4. Process according to claim 1 whereby the vinyl resin is polyvinyl chloride.

5. Process according to claim 1 whereby the vinyl resin is a vinyl chloride-vinyl acetate co-polymer.

6. Process according to claim 1 whereby the vinyl resin is a vinyl chloride-vinylidene chloride co-polymer.

7. Polymers and co-polymers of vinyl chloride containing at least one stabilizer according to claim 1.

8. Polymers and co-polymers of vinyl chloride containing at least one stabilizer according to claim 1 in a proportion of 0.01 to 1 part by 100 parts of resin by weight.

9. Polymers and co-polymers of vinyl chloride containing at least one stabilizer according to claim 1 in a proportion of 0.01 to 0.5 part by 100 parts of resin by weight.

* * * * *